(12) United States Patent
Xu et al.

(10) Patent No.: US 12,376,717 B2
(45) Date of Patent: Aug. 5, 2025

(54) ALLERGEN REDUCTION DEVICE

(71) Applicant: SHARKNINJA OPERATING LLC, Needham, MA (US)

(72) Inventors: Kai Xu, Suzhou (CN); Peter Hutchinson, Needham, MA (US)

(73) Assignee: SharkNinja Operating LLC, Needham, MA (US)

(*) Notice: Subject to any disclaimer, the term of this patent is extended or adjusted under 35 U.S.C. 154(b) by 261 days.

(21) Appl. No.: 17/961,067

(22) Filed: Oct. 6, 2022

(65) Prior Publication Data

US 2023/0025335 A1    Jan. 26, 2023

Related U.S. Application Data

(63) Continuation of application No. PCT/US2021/025894, filed on Apr. 6, 2021.

(Continued)

(51) Int. Cl.
*A47L 7/00* (2006.01)
*A46B 13/00* (2006.01)
(Continued)

(52) U.S. Cl.
CPC .............. *A47L 7/04* (2013.01); *A46B 13/005* (2013.01); *A46B 13/02* (2013.01); *A47L 5/26* (2013.01);
(Continued)

(58) Field of Classification Search
CPC . A47L 7/04; A47L 5/26; A47L 7/0061; A47L 9/0411; A47L 9/0477; A47L 9/127;
(Continued)

(56) References Cited

U.S. PATENT DOCUMENTS

| | | |
|---|---|---|
| 8,533,905 B1 | 9/2013 | Tran |
| 2003/0131439 A1 | 7/2003 | Wen |

(Continued)

FOREIGN PATENT DOCUMENTS

| | | |
|---|---|---|
| EP | 0251263 | 1/1988 |
| WO | 2016051968 | 4/2016 |
| WO | 2016181849 | 11/2016 |

OTHER PUBLICATIONS

PCT Search Report and Written Opinion, mailed Jul. 20, 2021, received in corresponding PCT Application No. PCT/US21/25894, 9 pages.

*Primary Examiner* — Katina N. Henson
(74) *Attorney, Agent, or Firm* — Grossman Tucker; Perreault & Pfleger PLLC

(57) ABSTRACT

An allergen reduction device may include a body, a dust cup removably coupled to the body, a plurality of agitators rotatably coupled to the body and disposed within respective agitator cavities defined in the body, a suction motor disposed within the body and configured to cause air to flow along corresponding cleaning airflow paths from the agitator cavities into the dust cup, a hot air outlet fluidly coupled to the suction motor, the suction motor being configured to urge the air through the hot air outlet along a heated exhaust airflow path, and a heater positioned within the heated exhaust airflow path between the suction motor and the hot air outlet, the heater being configured to heat the air that is urged from the hot air outlet.

17 Claims, 5 Drawing Sheets

Related U.S. Application Data

(60) Provisional application No. 63/005,838, filed on Apr. 6, 2020.

(51) Int. Cl.

| | | |
|---|---|---|
| *A46B 13/02* | (2006.01) | |
| *A47L 5/26* | (2006.01) | |
| *A47L 7/04* | (2006.01) | |
| *A47L 9/04* | (2006.01) | |
| *A47L 9/12* | (2006.01) | |
| *A47L 9/14* | (2006.01) | |
| *A47L 9/28* | (2006.01) | |
| *A61L 2/04* | (2006.01) | |
| *A61L 2/26* | (2006.01) | |

(52) U.S. Cl.
CPC ........... *A47L 7/0061* (2013.01); *A47L 9/0411* (2013.01); *A47L 9/0477* (2013.01); *A47L 9/127* (2013.01); *A47L 9/1409* (2013.01); *A47L 9/2889* (2013.01); *A61L 2/04* (2013.01); *A61L 2/26* (2013.01); *A46B 2200/3033* (2013.01); *A61L 2202/17* (2013.01); *A61L 2202/26* (2013.01)

(58) Field of Classification Search
CPC .. A47L 9/1409; A47L 9/2889; A47L 11/4069; A47L 25/00; A47L 9/28; A46B 13/005; A46B 13/02; A46B 2200/3033; A61L 2/04; A61L 2/26; A61L 2202/17; A61L 2202/26; D06F 58/30; D06F 58/00
USPC .......................................................... 15/339
See application file for complete search history.

(56) References Cited

U.S. PATENT DOCUMENTS

| | | | |
|---|---|---|---|
| 2006/0288495 A1 | 12/2006 | Sawalski et al. | |
| 2013/0058635 A1 | 3/2013 | Vrdoljak | |
| 2013/0152337 A1 | 6/2013 | Thorne | |
| 2014/0150201 A1 | 6/2014 | McGee et al. | |
| 2014/0259475 A1* | 9/2014 | Doughty | A47L 11/282 |
| | | | 15/207.2 |
| 2015/0013102 A1 | 1/2015 | Bilger | |
| 2015/0040340 A1 | 2/2015 | Bilger et al. | |
| 2015/0135474 A1 | 5/2015 | Gidwell | |
| 2015/0297054 A1 | 10/2015 | Weeks et al. | |
| 2015/0351596 A1 | 12/2015 | Thorne | |
| 2016/0051111 A1 | 2/2016 | Lee | |
| 2016/0128530 A1 | 5/2016 | Thorne et al. | |
| 2016/0174793 A1 | 6/2016 | Burke et al. | |
| 2016/0220080 A1 | 8/2016 | Thorne | |
| 2016/0220081 A1 | 8/2016 | Xu et al. | |
| 2016/0220082 A1 | 8/2016 | Thorne et al. | |
| 2016/0324388 A1 | 11/2016 | Vrdoljak et al. | |
| 2016/0374533 A1 | 12/2016 | Innes et al. | |
| 2017/0042319 A1 | 2/2017 | Conrad et al. | |
| 2017/0112343 A1 | 4/2017 | Innes et al. | |
| 2017/0127896 A1 | 5/2017 | Carter et al. | |
| 2017/0144810 A1 | 5/2017 | Birdsell | |
| 2017/0215667 A1 | 8/2017 | Thorne et al. | |
| 2017/0347848 A1 | 12/2017 | Carter et al. | |
| 2018/0035854 A1 | 2/2018 | Thorne | |
| 2018/0064301 A1 | 3/2018 | Cottrell et al. | |
| 2018/0068815 A1 | 3/2018 | Cottrell | |
| 2018/0070785 A1 | 3/2018 | Udy et al. | |
| 2018/0255991 A1 | 9/2018 | Der Marderosian et al. | |
| 2018/0296046 A1 | 10/2018 | Thorne et al. | |
| 2018/0306432 A1 | 10/2018 | Ognjen et al. | |
| 2018/0325252 A1 | 11/2018 | Hopke et al. | |
| 2018/0338654 A1 | 11/2018 | Kelsey | |
| 2018/0338656 A1 | 11/2018 | Carter et al. | |
| 2019/0038098 A1 | 2/2019 | Thorne et al. | |
| 2019/0059668 A1 | 2/2019 | Thorne et al. | |
| 2019/0069740 A1 | 3/2019 | Thorne et al. | |
| 2019/0069744 A1 | 3/2019 | Liggett et al. | |
| 2019/0090701 A1 | 3/2019 | Tonderys et al. | |
| 2019/0090705 A1 | 3/2019 | Thorne et al. | |
| 2019/0191947 A1 | 6/2019 | Freese et al. | |
| 2019/0193120 A1 | 6/2019 | Brown et al. | |
| 2019/0246853 A1 | 8/2019 | Sardar et al. | |
| 2019/0274500 A1 | 9/2019 | Thorne et al. | |
| 2019/0274501 A1 | 9/2019 | Antonisami et al. | |
| 2019/0302793 A1 | 10/2019 | Leech et al. | |
| 2019/0320865 A1 | 10/2019 | Brown et al. | |
| 2019/0320866 A1 | 10/2019 | Thorne et al. | |
| 2019/0335968 A1 | 11/2019 | Harting et al. | |
| 2019/0343349 A1 | 11/2019 | Clare et al. | |
| 2019/0357740 A1 | 11/2019 | Thorne et al. | |
| 2020/0000298 A1 | 1/2020 | Brown et al. | |
| 2020/0022543 A1 | 1/2020 | Gill et al. | |
| 2020/0022544 A1 | 1/2020 | Gill et al. | |
| 2020/0022553 A1 | 1/2020 | Gill et al. | |
| 2020/0037833 A1 | 2/2020 | Niedzwecki et al. | |
| 2020/0037843 A1 | 2/2020 | Fiebig et al. | |
| 2020/0046184 A1 | 2/2020 | Freese et al. | |
| 2020/0077855 A1 | 3/2020 | Brown et al. | |
| 2020/0085267 A1 | 3/2020 | Thorne et al. | |
| 2020/0085269 A1 | 3/2020 | Thorne | |
| 2020/0121144 A1 | 4/2020 | Gacin et al. | |
| 2020/0121148 A1 | 4/2020 | Hoffman et al. | |
| 2020/0138260 A1 | 5/2020 | Sutter et al. | |
| 2020/0166949 A1 | 5/2020 | Leech et al. | |
| 2020/0170470 A1 | 6/2020 | Liggett et al. | |
| 2020/0201348 A1 | 6/2020 | Leech | |
| 2020/0205631 A1 | 7/2020 | Brown et al. | |
| 2020/0205634 A1 | 7/2020 | Sutter et al. | |
| 2020/0237171 A1 | 7/2020 | Xu et al. | |
| 2020/0288929 A1 | 9/2020 | Brunner | |
| 2020/0288930 A1 | 9/2020 | Wells | |
| 2020/0297172 A1 | 9/2020 | Tonderys et al. | |
| 2020/0301430 A1 | 9/2020 | Irkliy et al. | |
| 2020/0315418 A1 | 10/2020 | Howard et al. | |
| 2020/0345196 A1 | 11/2020 | Innes et al. | |
| 2020/0367711 A1 | 11/2020 | Thorne et al. | |
| 2020/0371526 A1 | 11/2020 | Kamada | |
| 2020/0383547 A1 | 12/2020 | Sutter et al. | |
| 2021/0007569 A1 | 1/2021 | Howard et al. | |
| 2021/0022574 A1 | 1/2021 | Harting | |
| 2021/0030227 A1 | 2/2021 | Mathieu et al. | |
| 2021/0038032 A1 | 2/2021 | Brown | |
| 2021/0059495 A1 | 3/2021 | Gill et al. | |
| 2021/0085144 A1 | 3/2021 | Woodrow et al. | |
| 2021/0169289 A1 | 6/2021 | Thorne et al. | |
| 2021/0175772 A1 | 6/2021 | Aini | |
| 2021/0177223 A1 | 6/2021 | Der Marderosian et al. | |
| 2021/0186282 A1 | 6/2021 | Mathieu et al. | |
| 2021/0204684 A1 | 7/2021 | Heman-Ackah et al. | |
| 2021/0254615 A1 | 8/2021 | Burbank | |
| 2021/0307581 A1 | 10/2021 | Thorne et al. | |
| 2021/0315428 A1 | 10/2021 | Udy et al. | |
| 2021/0386261 A1 | 12/2021 | Woodrow et al. | |
| 2021/0386262 A1 | 12/2021 | Uchendu et al. | |
| 2022/0031131 A1 | 2/2022 | McClay et al. | |
| 2022/0031133 A1 | 2/2022 | Der Marderosian et al. | |
| 2022/0031134 A1 | 2/2022 | Yang et al. | |
| 2022/0061614 A1 | 3/2022 | Yu et al. | |
| 2022/0071459 A1 | 3/2022 | Gacin et al. | |
| 2022/0095864 A1 | 3/2022 | Der Marderosian et al. | |
| 2022/0125256 A1 | 4/2022 | Lessard et al. | |
| 2022/0192451 A1 | 6/2022 | Li et al. | |
| 2022/0287521 A1 | 9/2022 | Cottrell et al. | |
| 2022/0322903 A1 | 10/2022 | Lessard | |
| 2022/0400922 A1 | 12/2022 | McClay et al. | |
| 2022/0408994 A1 | 12/2022 | Hill | |
| 2023/0043567 A1 | 2/2023 | Copeland et al. | |
| 2023/0070147 A1 | 3/2023 | Harting et al. | |
| 2023/0157495 A1 | 5/2023 | Copeland et al. | |
| 2023/0248192 A1 | 8/2023 | Brown et al. | |
| 2023/0329502 A1 | 10/2023 | Chirikjian | |
| 2024/0415352 A1 | 12/2024 | McClay et al. | |

* cited by examiner

ALLERGEN REDUCTION DEVICE

CROSS-REFERENCE TO RELATED APPLICATIONS

The present application is a Continuation Application of PCT Application No. PCT/US21/25894 filed Apr. 6, 2021, which claims the benefit of U.S. Provisional Application Ser. No. 63/005,838 filed on Apr. 6, 2020, entitled Allergen Reduction Device, both of which are fully incorporated herein by reference.

TECHNICAL FIELD

The present disclosure is generally directed to a device configured to reduce a quantity of household allergens and more specifically directed to a device configured to reduce a quantity of allergens found in household objects such as, for example, bedding.

BACKGROUND INFORMATION

Household allergens can cause distress to occupants within the household. Household allergens may include, for example, dust, dander, and mites. Some household allergens may reside in household objects such as, for example, bedding, furniture coverings (e.g., of chairs, mattresses, etc.), blinds, and/or any other household object. Some of these household objects may not be easily cleaned given the size of the household object or location of the household object.

BRIEF DESCRIPTION OF THE DRAWINGS

These and other features and advantages will be better understood by reading the following detailed description, taken together with the drawings, wherein.

DETAILED DESCRIPTION

The present disclosure is generally directed to an allergen reduction device. The allergen reduction device includes a body including a suction motor, a dust cup, at least one agitator (e.g., a rotatable component having flaps and/or bristles extending from a body thereof), and a heated air outlet. The suction motor is configured to cause suction to be generated at the agitator such that air flows from a surrounding environment over the agitator, into the dust cup, into the suction motor, and out the heated air outlet. A heater is positioned between the suction motor and the heated air outlet such that air exiting the suction motor is heated by the heater before passing through the heated air outlet.

In operation, the allergen reduction device can be moved along an object comprising one or more materials (e.g., a quilt comprising at least a fabric outer material and an inner filling material) that potentially contains allergens (e.g., dust, dander, mites, and/or the like). The agitator can disturb allergens in the object such that they can be suctioned into the dust cup. The heated air passing through the heated air outlet can come into contact with and penetrate through at least a portion of the object, killing, for example, mites present in the object. As such, the allergen reduction device may reduce dust, dander, and/or mites that are present in and/or on an object. Additionally, or alternatively, the heated air may kill viruses and bacteria present on the object.

Figure 1:
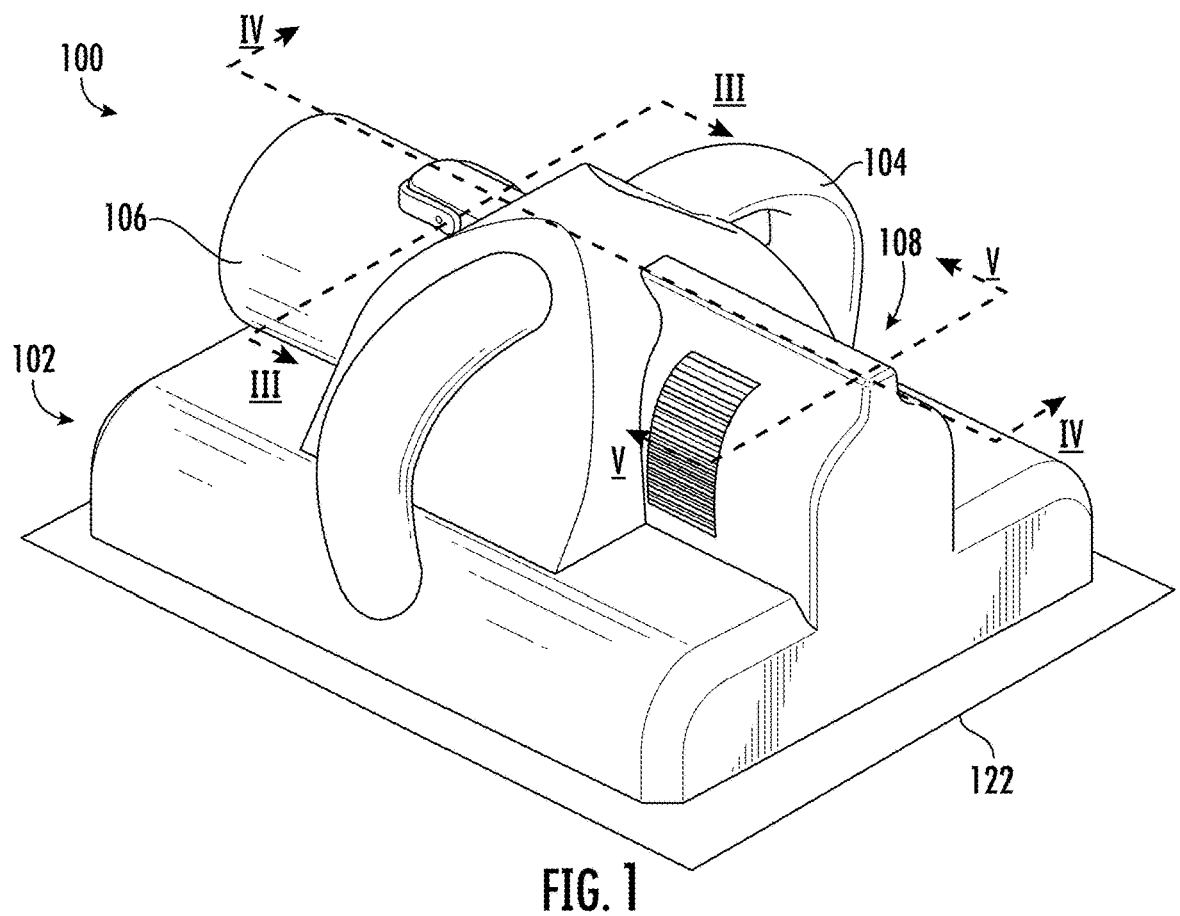
FIG. 1 is a perspective top view of an allergen reduction device, consistent with embodiments of the present disclosure.
Figure 2:
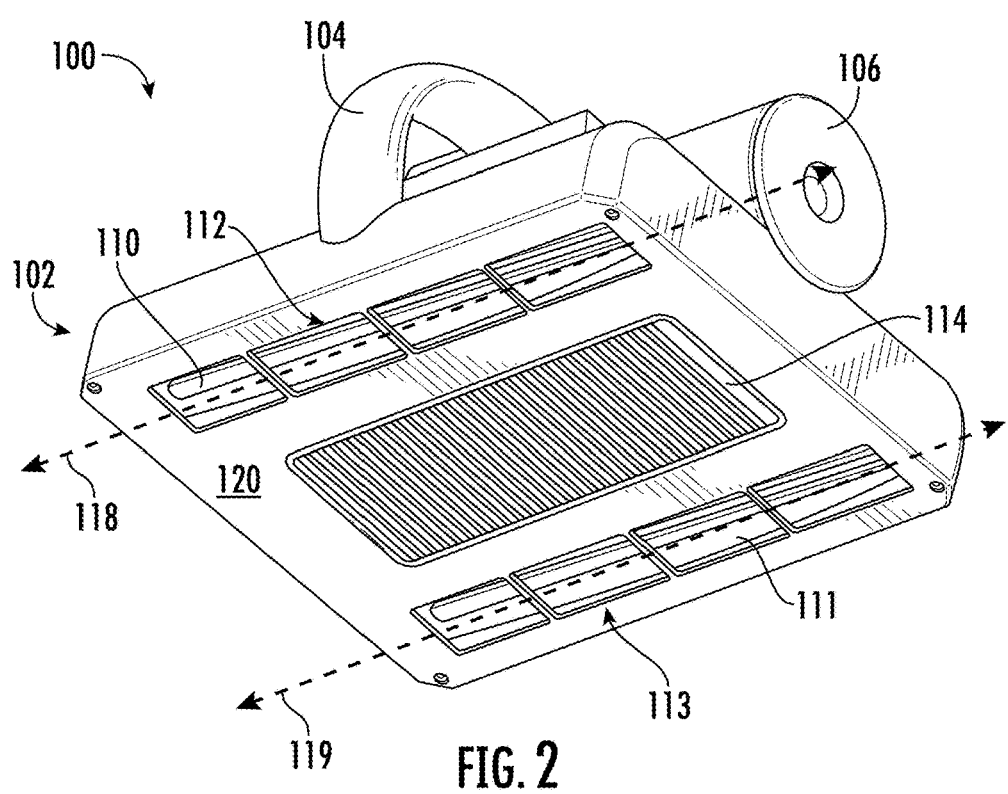
FIG. 2 is a perspective bottom view of the allergen reduction device of FIG. 1, consistent with embodiments of the present disclosure.

FIG. 1 shows a perspective top view of an example of an allergen reduction device 100 and FIG. 2 shows a perspective bottom view of the allergen reduction device 100. As shown, the allergen reduction device 100 includes a body 102 having one or more handles 104, a dust cup 106 removably coupled to the body 102, a suction motor 108 disposed within the body 102, a plurality of agitators 110 and 111 rotatably disposed within respective agitator cavities 112 and 113 defined in the body 102, and a hot air outlet 114 fluidly coupled to the suction motor 108 and defined in the body 102 at a location between the plurality of agitators 110 and 111.

The plurality of agitators 110 and 111 extend within respective agitator cavities 112 and 113 along corresponding rotation axes 118 and 119. The rotation axes 118 and 119 can extend substantially parallel (e.g., within at least 15 degrees of parallel, within at least 10 degrees of parallel, within at least 5 degrees of parallel, or within at least 1 degree of parallel) to each other and substantially parallel to a sliding surface 120 of the body 102. The plurality of agitators 110 and 111 can be configured to be counter rotating. In other words, the first agitator 110 can rotate about the first rotation axis 118 according to a first rotation direction (e.g., clockwise) and the second agitator 111 can be configured to rotate about the second rotation axis 119 according to a second rotation direction (e.g., counter clockwise), wherein the first and second rotation directions are opposite. For example, each of the agitators 110 and 111 can be configured to rotate in a direction away from the hot air outlet 114. In this example, the counter rotation of the agitators 110 and 111 would encourage a stretching of an object 122 (e.g., a fabric) that is in engagement (e.g., contact) with or positioned beneath the sliding surface 120 of the body 102.

Figure 3:
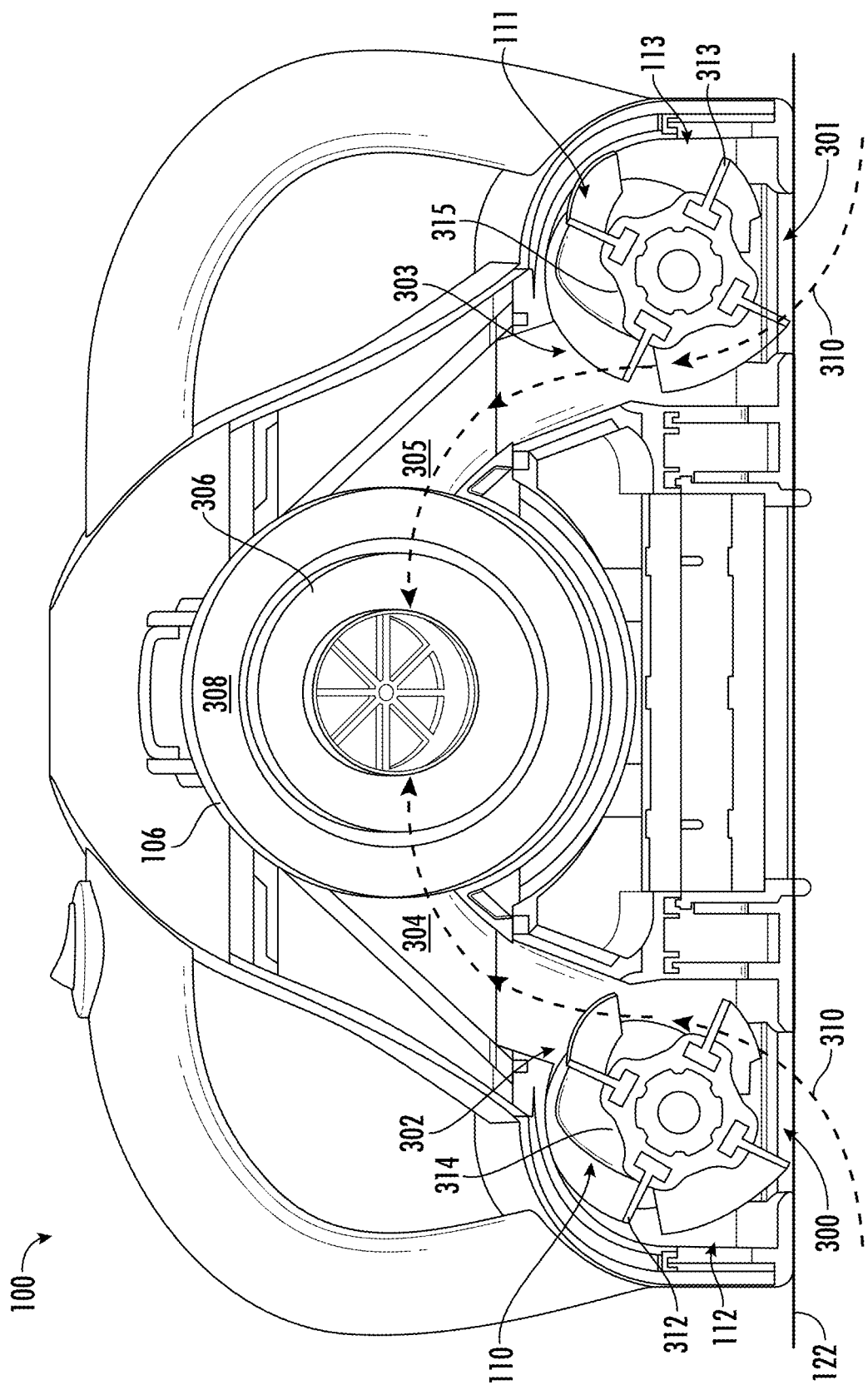
FIG. 3 is a cross-sectional view of the allergen reduction device of FIG. 1 taken along the line III-III of FIG. 1, consistent with embodiments of the present disclosure.

FIG. 3 shows a cross-sectional view of the allergen reduction device 100 taken along the line III-III of FIG. 1. As shown, the agitator cavities 112 and 113 each include a respective air inlet 300 and 301 and air outlet 302 and 303, which are fluidly coupled to the suction motor 108. At least a portion of each agitator 110 and 111 may extend from respective air inlets 300 and 301 such that each agitator 110 and 111 may engage (e.g., contact) the object 122 that is engaging or extending beneath the sliding surface 120. For example, the agitators 110 and 111 may each include one or more flaps 312 and 313 that extend from an agitator body 314 and 315 of the agitators 110 and 111 such that the flaps 312 and 313 (e.g., rubber flaps) engage the object 122. Use of the flaps 312 and 313, instead of bristles, may reduce power consumption and/or may reduce a wrapping of a portion of the object 122 (e.g., a fabric covering of the household object 122 or a sheet) about the agitators 110 and 111. However, in some instances, the agitators 110 and 111 may include bristles in addition to, or in the alternative to, the flaps 312 and 313.

The engagement between the agitators 110 and 111 and the object 122 engaging or extending beneath the sliding surface 120 may cause allergens on or within the object 122 to be agitated in response to rotation of the agitators 110 and 111. The agitated allergens may become entrained within air being suctioned through the air inlets 300 and 301 such that the entrained allergens pass into the respective air outlets 302 and 303.

The air outlets 302 and 303 are fluidly coupled to respective channels 304 and 305. The channels 304 and 305 are fluidly coupled to the dust cup 106. A filter 306 extends within a collection cavity 308 of the dust cup 106. The filter 306 is configured to cause at least a portion of the allergens entrained within the air flowing into the dust cup 106 to become separated from the air. As such, at least a portion of the entrained allergens may be collected within the dust cup 106 and/or the filter 306. Accordingly, air flowing from the air inlets 300 and 301 and through the filter 306 may generally be described as flowing along one or more (e.g., a plurality of) cleaning airflow paths 310. For example, and as shown, there may be a plurality of cleaning air flow paths 310, each corresponding to a respective agitator cavity 112 and 113, wherein the cleaning airflow paths 310 converge (e.g., combine) at the dust cup 106. By way of further example, in some instances, the cleaning airflow path 310 may extend through at least one of the agitator cavities 112 and/or 113. In this example, the cleaning airflow path 310 may extend through only one of the agitator cavities 112 or 113. As such, the suction motor 108 can generally be described as being configured to cause air to flow along the cleaning airflow path 310 through the one or more agitator cavities 112 and/or 113 and into the dust cup 106.

The filter 306 may be a high efficiency particulate air (HEPA) filter. For example, the filter 306 may be a glass fabric HEPA filter.

Figure 4:
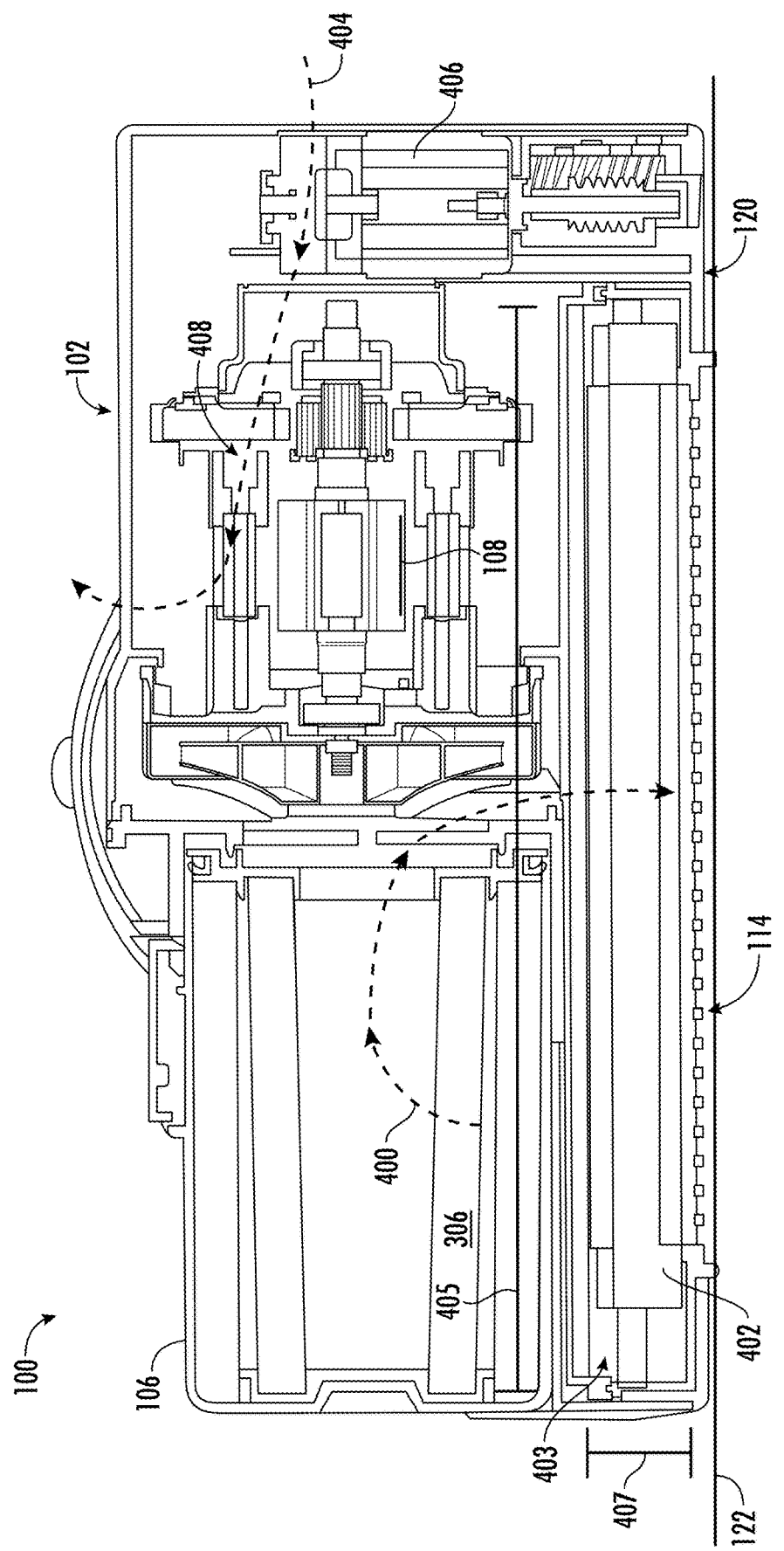
FIG. 4 is a cross-sectional view of the allergen reduction device of FIG. 1 taken along the line IV-IV of FIG. 1, consistent with embodiments of the present disclosure.

FIG. 4 shows a cross-sectional view of the allergen reduction device 100 taken along the line IV-IV of FIG. 1. As shown, the dust cup 106 is fluidly coupled to the suction motor 108 through the filter 306. Air drawn through filter 306 and into the suction motor 108 is urged by the suction motor 108 through the hot air outlet 114. Accordingly, air flowing from the filter 306 into the suction motor 108 and out the hot air outlet 114 may generally be described as flowing along a heated exhaust airflow path 400. Air flowing along the heated exhaust airflow path 400 and the cleaning airflow path 310 may generally be referred to as cleaning air.

A heater 402 is positioned within the heated exhaust airflow path 400 at a location between the suction motor 108 and the hot air outlet 114 such that air passes through the heater 402 before passing through the hot air outlet 114. As a result, the heater 402 causes air passing through the heater 402 to be heated to a predetermined temperature before being exhausted from the hot air outlet 114. The predetermined temperature may be, for example, within a range of 100 degrees Celsius to 140 degrees Celsius. By way of further example, the predetermined temperature may be 120 degrees Celsius. The heater 402 may, for example, include a positive temperature control material configured to generate heat. Additionally, or alternatively, the heater 402 may include one or more resistive elements configured to generate heat. The heater 402 may be an 800 watt (W) to 1200 W heater. In some instances, the heater 402 can be configured to operate in absence of air flowing along the heated exhaust airflow path 400.

The heater 402 may be at least partially thermally isolated from the one or more handles 104 such that a user of the allergen reduction device 100 does not experience discomfort while using the allergen reduction device 100 as a result of heat generated by the heater 402. As shown, the heater 402 is disposed within a hot air tunnel 403. The hot air tunnel 403 may be made of heat tolerant material, such as polybutylene terephthalate, which may be a different material from the remainder of the body 102. The hot air tunnel 403 has a hot air tunnel length 405 (e.g., a longitudinal length) and a hot air tunnel height 407 extending vertically in a direction away from the sliding surface 120. The hot air tunnel length 405 multiplied by the hot air tunnel height 407 (or a cross-sectional area) may measure in, for example, a range of 400 square millimeters ($mm^2$) to 2000 $mm^2$. By way of further example, the cross-sectional area of the hot air tunnel 403 may measure about (e.g., within +/−15% of) 600 $mm^2$.

The suction motor 108 can be configured to generate a sufficient suction force to cause the air exhausted from the hot air outlet 114 to penetrate a predetermined depth into the object 122 engaging or extending beneath the sliding surface 120. For example, the suction motor 108 may be configured generate at least 12 kilopascals (KPa) of suction. A suction force of at least 12 KPa may cause air exhausted from the hot air outlet 114 to penetrate at least through a 2.54 centimeter (cm) cotton quilt. The object 122 can be considered to be penetrated to a predetermined depth if, at the predetermined depth, a temperature of the object 122 measures at least 80 degrees Celsius. The suction motor 108 may be a 500 W to 600 W suction motor.

The hot air exhausted from the hot air outlet 114 may urge the allergen reduction device 100 in a direction away from the object 122. This may make movement along the object 122 easier by reducing a frictional force between the allergen reduction device 100 and the object 122. In some instances, the hot air exhausted from the hot air outlet 114 may urge at least a portion of the sliding surface 120 out of engagement with the object 122, while the agitators 110 and 111 remain in contact with the object 122. As such, in these instances, the hot air being exhausted from the hot air outlet 114 may generally be described as causing at least a portion of the allergen reduction device 100 to float relative to the object 122.

The suction motor 108 may be cooled using cooling air that flows along a cooling airflow path 404. The cooling airflow path 404 can extend through the suction motor 108 and/or an agitator motor 406. The cooling airflow path 404 can be separate from both the cleaning airflow path 310 and the heated exhaust airflow path 400. For example, and as shown, the cooling airflow path 404 can extend from the environment through the agitator motor 406 into cooling channels 408 of the suction motor 108 and back into the environment. The cooling channels 408 may include a wall extending therein that separates the cooling airflow path 404 from the cleaning airflow path 310 and the heated exhaust airflow path 400. In some instances, the suction motor 108 can be configured to cause cooling air to flow along the cooling airflow path 404. For example, the suction motor 108 may include a first fan/impeller configured to cause air to flow along the cleaning airflow path 310 and the heated exhaust airflow path 400 and a second fan/impeller configured to cause air to flow along the cooling airflow path 404.

Having the cooling airflow path 404 separate from the cleaning airflow path 310 and the exhaust airflow path 400 may encourage more efficient cooling of the suction motor 108 and/or prevent damage to the suction motor 108 caused by insufficient cooling. In some instances, at least a portion of the air drawn into the air inlets 300 and 301 may be preheated by and/or include air exhausted from the hot air outlet 114, which may increase the efficiency at which air is heated by the heater 402. In other words, the cleaning airflow path 310 and the exhaust airflow path 400 may generally be described as forming a recirculation loop in which air circulates from the hot air outlet 114 to the air inlets 300 and 301. In these instances, the filter 306 may be a glass fiber HEPA filter, which may allow the filter 306 to perform more consistently while being exposed to an increased air temperature in the recirculation loop.

Figure 5:
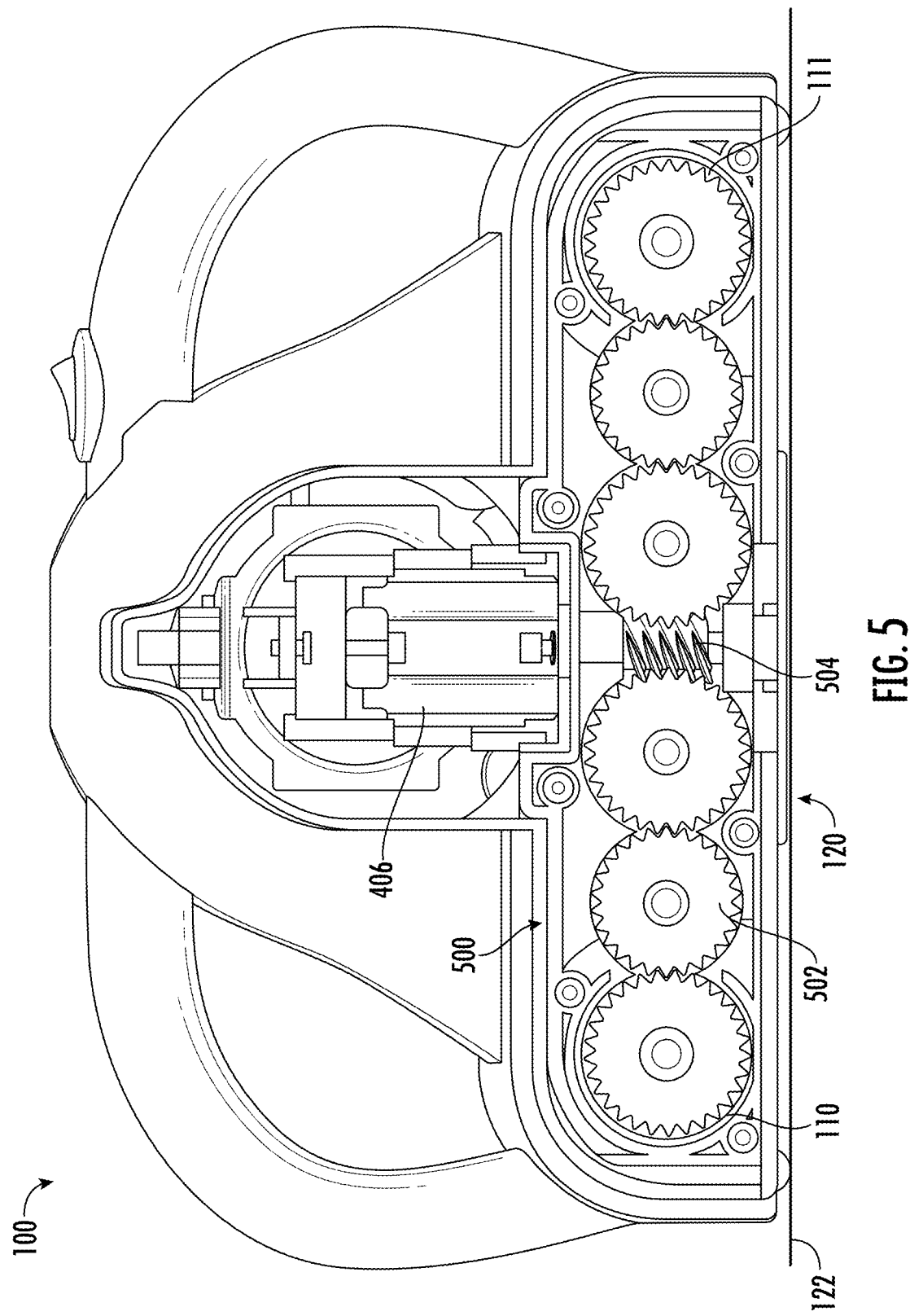
FIG. 5 is a cross-sectional view of the allergen reduction device of FIG. 1 taken along the line V-V of FIG. 1, consistent with embodiments of the present disclosure.

FIG. 5 shows a cross-sectional view of the allergen reduction device 100 taken along the line V-V of FIG. 1. As shown, the agitator motor 406 is configured to cause both agitators 110 and 111 to rotate (or drive the agitators 110 and 111). For example, the agitator motor 406 may be coupled to a drive train 500 configured to cause each of the agitators 110 and 111 to rotate in opposing directions. In other words, the drive train 500 can be configured such that the agitators 110 and 111 are counter rotating. Counter rotating agitators 110 and 111 may cause a surface of the object 122 (e.g., a fabric outer surface) to be stretched such that the object 122 does not become entangled in the agitators 110 and 111 and/or such that the surface of the object 122 is substantially parallel (e.g., within at least 15 degrees of parallel, within at least 10 degrees of parallel, within at least 5 degrees of parallel, or within at least 1 degree of parallel) to the sliding surface 120.

The drive train 500 may include a plurality of worm gears 502 disposed on opposing sides of a worm 504 such that rotation of the worm 504 causes a corresponding rotation in the worm gears 502. The drive train 500 may be a reduction drive train in which the rate of rotation of the agitators 110 and 111 measures less than the rate of rotation of a drive shaft of the agitator motor 406. For example, the agitator motor 406 may be a 50 W motor having a drive shaft rotation speed of 11,000 revolutions per minute (RPM) and the drive train 500 may be configured such that the agitators 110 and 111 rotate at 1000 RPM.

Figure 6:
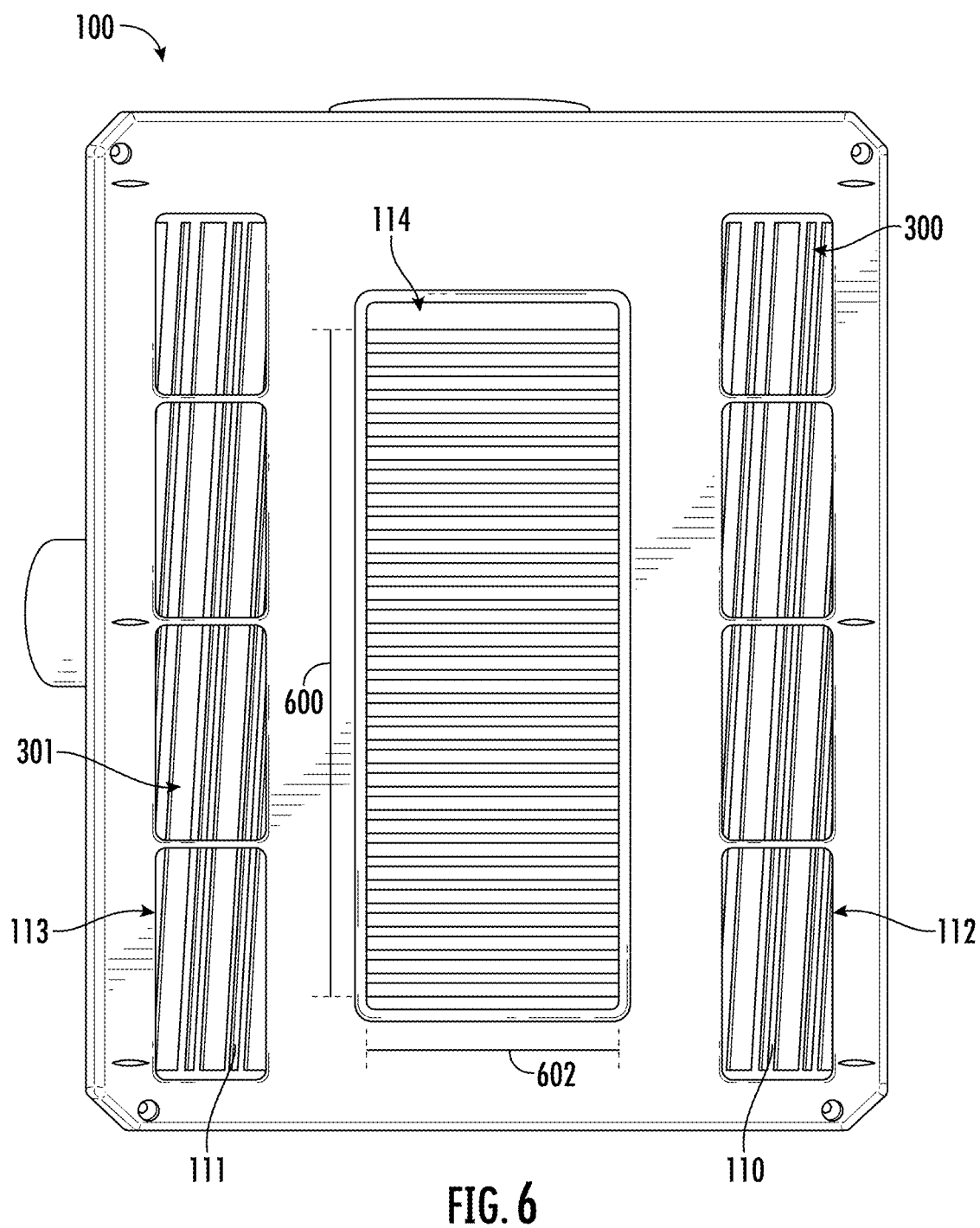
FIG. 6 is a bottom view of the allergen reduction device of FIG. 1, consistent with embodiments of the present disclosure.

FIG. 6 shows a bottom view of the allergen reduction device 100. As shown, the hot air outlet 114 extends longitudinally between the agitators 110 and 111 and is spaced apart from the air inlets 300 and 301 of the agitator cavities 112 and 113. A length 600 of the hot air outlet 114 may measure, for example, at least twice a width 602 of the hot air outlet 114.

An example of an allergen reduction device, consistent with the present disclosure, may include a body, a dust cup removably coupled to the body, a plurality of agitators rotatably coupled to the body and disposed within respective agitator cavities defined in the body, a suction motor disposed within the body and configured to cause cleaning air to flow along corresponding cleaning airflow paths from the agitator cavities into the dust cup, a hot air outlet fluidly coupled to the suction motor, the suction motor being configured to urge the cleaning air through the hot air outlet along a heated exhaust airflow path, and a heater positioned within the heated exhaust airflow path between the suction motor and the hot air outlet, the heater being configured to heat the cleaning air that is urged from the hot air outlet.

In some instances, the hot air outlet may be disposed between the plurality of agitators. In some instances, the agitators may be counter rotating. In some instances, a filter may extend within the dust cup. In some instances, the filter may be a high efficiency particulate air (HEPA) filter. In some instances, the filter may be a glass fabric HEPA filter.

In some instances, the suction motor may be further configured to cause cooling air to flow along a cooling airflow path, wherein the cooling airflow path extends through the suction motor. In some instances, the cooling airflow path may be separate from the cleaning airflow paths and the heated exhaust airflow path. In some instances, the allergen reduction device may further include an agitator motor configured to cause the plurality of agitators to rotate. In some instances, each of the agitators may include one or more flaps. In some instances, the heater may be configured to heat the cleaning air passing therethrough to a temperature in a range of 100 degrees Celsius to 140 degrees Celsius. In some instances, the heater may be disposed within a hot air tunnel. In some instances, the hot air tunnel may have a cross-sectional area measuring in a range of 400 square millimeters to 2000 square millimeters.

Another example of an allergen reduction device, consistent with the present disclosure, may include a body, a plurality of agitators rotatably coupled to the body and disposed within respective agitator cavities defined in the body, a suction motor disposed within the body and configured to cause air to flow along a cleaning airflow path that extends through at least one of the agitator cavities, a hot air outlet fluidly coupled to the suction motor, the suction motor being configured to urge the air through the hot air outlet along a heated exhaust airflow path, and a heater positioned within the heated exhaust airflow path between the suction motor and the hot air outlet, the heater being configured to heat the air that is urged from the hot air outlet.

In some instances, the hot air outlet may be disposed between the plurality of agitators. In some instances, the agitators may be counter rotating. In some instances, each of the agitators may include one or more flaps. In some instances, the heater may be configured to heat the air passing therethrough to a temperature in a range of 100 degrees Celsius to 140 degrees Celsius. In some instances, the heater may be disposed within a hot air tunnel. In some instances, the hot air tunnel may have a cross-sectional area measuring in a range of 400 square millimeters to 2000 square millimeters.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. An allergen reduction device comprising:
 a body having a sliding surface that is configured to be moveable along an object;
 a dust cup removably coupled to the body;
 a first agitator rotatably coupled to the body and disposed within a first agitator cavity defined in the body, the first agitator being configured to contact the object;
 a second agitator rotatably coupled to the body and disposed within a second agitator cavity defined in the body, the second agitator being configured to contact the object, wherein the first and second agitators are configured to counter rotate to stretch the object such that a portion of the object extending between the agitators is substantially parallel to the sliding surface of the body;

a suction motor disposed within the body and configured to cause cleaning air to flow along corresponding cleaning airflow paths from the first and second agitator cavities into the dust cup;

a hot air outlet fluidly coupled to the suction motor, the suction motor being configured to urge the cleaning air along a heated exhaust airflow path and through the hot air outlet such that the heated exhaust airflow path intersects the object after exiting the hot air outlet, wherein the hot air outlet is disposed between the first and second agitators such that the cleaning air exiting the hot air outlet urges the sliding surface of the body in a direction away from the object; and a heater positioned within the heated exhaust airflow path between the suction motor and the hot air outlet, the heater being configured to heat the cleaning air that is urged from the hot air outlet.

2. The allergen reduction device of claim 1, wherein a filter extends within the dust cup.

3. The allergen reduction device of claim 2, wherein the filter is a high efficiency particulate air (HEPA) filter.

4. The allergen reduction device of claim 3, wherein the filter is a glass fabric HEPA filter.

5. The allergen reduction device of claim 1, wherein the suction motor is further configured to cause cooling air to flow along a cooling airflow path, wherein the cooling airflow path extends through the suction motor.

6. The allergen reduction device of claim 5, wherein the cooling airflow path is separate from the cleaning airflow paths and the heated exhaust airflow path.

7. The allergen reduction device of claim 1 further comprising an agitator motor configured to cause the first and second agitators to rotate.

8. The allergen reduction device of claim 1, wherein each of the first and second agitators include one or more flaps.

9. The allergen reduction device of claim 1, wherein the heater is configured to heat the cleaning air passing therethrough to a temperature in a range of 100 degrees Celsius to 140 degrees Celsius.

10. The allergen reduction device of claim 1, wherein the heater is disposed within a hot air tunnel.

11. The allergen reduction device of claim 10, wherein the hot air tunnel has a cross-sectional area measuring in a range of 400 square millimeters to 2000 square millimeters.

12. An allergen reduction device comprising:

a body having a sliding surface configured to be moveable along an object;

a first agitator rotatably coupled to the body and disposed within a first agitator cavity defined in the body;

a second agitator rotatably coupled to the body and disposed within a second agitator cavity defined in the body, the second agitator being configured to contact the object, wherein the first and second agitators are configured to counter rotate to stretch the object such that a portion of the object extending between the agitators is substantially parallel to the sliding surface of the body;

a suction motor disposed within the body and configured to cause air to flow along a cleaning airflow path that extends through at least one of the first or second agitator cavities;

a hot air outlet fluidly coupled to the suction motor, the suction motor being configured to urge the air along a heated exhaust airflow path that extends through the hot air outlet; and a heater positioned within the heated exhaust airflow path between the suction motor and the hot air outlet, the heater being configured to heat the air that is urged from the hot air outlet.

13. The allergen reduction device of claim 12, wherein the heated exhaust airflow path intersects the object after exiting the hot air outlet and the hot air outlet is disposed between the first and second agitators such that the cleaning air exiting the hot air outlet urges the sliding surface of the body in a direction away from the object.

14. The allergen reduction device of claim 12, wherein each of the agitators include one or more flaps.

15. The allergen reduction device of claim 12, wherein the heater is configured to heat the air passing therethrough to a temperature in a range of 100 degrees Celsius to 140 degrees Celsius.

16. The allergen reduction device of claim 12, wherein the heater is disposed within a hot air tunnel.

17. The allergen reduction device of claim 16, wherein the hot air tunnel has a cross-sectional area measuring in a range of 400 square millimeters to 2000 square millimeters.

* * * * *